United States Patent [19]
Anstice et al.

[11] Patent Number: 5,601,640
[45] Date of Patent: Feb. 11, 1997

[54] COMMAND-CURABLE COMPOSITION

[75] Inventors: Helen M. Anstice, London; John W. Nicholson, Hampton, both of England

[73] Assignee: British Technology Group Limited, London, England

[21] Appl. No.: 403,861

[22] PCT Filed: Nov. 1, 1993

[86] PCT No.: PCT/GB87/00085

§ 371 Date: Mar. 23, 1995

§ 102(e) Date: Mar. 23, 1995

[87] PCT Pub. No.: WO88/05651

PCT Pub. Date: Aug. 11, 1988

[30] Foreign Application Priority Data

Nov. 4, 1992 [GB] United Kingdom ............... 9223068

[51] Int. Cl.⁶ .................... A61K 6/08; A61K 6/06
[52] U.S. Cl. ............ 106/35; 433/228.1; 523/116; 523/115; 526/278; 524/547
[58] Field of Search ................ 106/35; 433/228.1; 523/116, 115; 524/547; 526/278

[56] References Cited

U.S. PATENT DOCUMENTS

| | | | |
|---|---|---|---|
| 4,259,117 | 3/1981 | Yamauchi et al. | 523/116 |
| 5,204,426 | 4/1993 | Elis et al. | 523/116 |

FOREIGN PATENT DOCUMENTS

| | | |
|---|---|---|
| 0323120 | 7/1989 | European Pat. Off. |
| 0395427 | 10/1990 | European Pat. Off. |
| WO88/05651 | 8/1988 | WIPO |
| 88/5651 | 8/1988 | WIPO |

*Primary Examiner*—Melissa Bonner
*Attorney, Agent, or Firm*—Nixon & Vanderhye

[57] ABSTRACT

A light-curable dental cement composition contains (a) the reaction product of vinyl phosphonyl chloride and pentane 1,5 diol, (b) a photopolymerisation initiator, (c) ion-leachable aluminosilicate glass powder, (d) poly(vinyl phosphonic acid), (e) bisGMA as a photopolymerisable dimethacrylate resin, and water, inert filler and silanising agent. Upon mixing, glass is added last, the composition is put in place and, when ready, it is light-irradiated for 30 or 40 seconds to polymerise (e). The composition is immediately firm and the phosphonate groups adhere to tooth material while further slow curing by acid-base reaction continues.

14 Claims, No Drawings

COMMAND-CURABLE COMPOSITION

This invention relates to compositions curable on command, e.g. by the action of incident energy e.g. light (ultraviolet or visible) or ultrasound. Such compositions may contain inert or reactive fillers, in which case they can be classed as cements, and may be particularly useful in surgical, especially dental, applications.

As dental cements, glass ionomers as described in for example GB Patents 1422337 and 1484454 have attained wide popularity for their compressive strength, their inherent adhesion to tooth material, their relatively fast setting time and their anti-caries action. However, a drawback in clinical practice is that, once mixed, the glass ionomer cement composition stays workable for a strictly limited time only, and sets rapidly.

It has been proposed in EP-A-323120 to formulate a glass ionomer with modifying agents to delay its setting, with photocurable characteristics too, so that a photocure can be effected by the dentist when he is ready, with the acid-base glass ionomer reaction proceeding in parallel. However, those formulations having acceptable adhesiveness remain workable for only about five minutes, which could still be too short to deal with unexpected clinical eventualities.

Nonetheless, light-cured glass-ionomer cements have now become widely available for use as lining materials. The photocurable characteristics are supplied by adding, to the glass and polyacid required for the acid-base reaction, polymerisable monomers such as hydroxyethylmethacrylate (HEMA) which participate in the photopolymerisation reaction.

These light-cured glass-ionomers have proved to be very sensitive to the presence of moisture. This is because the set cement has a structure similar to that of a hydrogel. The structure is lightly crosslinked and contains hydrophilic groups, the light-cured methacrylates. Hence the cement has an affinity for water, which, once absorbed, acts as a plasticiser within the materials and reduces the strength of the cement. The water also tends to swell the cement.

WO-A-88/05651 discloses a light-curable glass ionomer lining material detectable by X-rays, comprising a fluoroaluminosilicate glass, barium glass, benzoyl peroxide and a resinous binder particularly bis-GMA or urethane dimethacrylate. This WO lists desirable criteria which this liner should meet as including translucency, formulation as a two-paste system, long shelf life, low solubility in oral fluids, strong adhesion to tooth, suitable working and setting times, and adequate strength.

EP-A-0 395 427 discloses a phosphonate ester which will cure on exposure to light in the presence of an initiator, this being mixed with poly(vinyl phosphonic acid), glass powder and water, to form a light-curable glass ionomer as already mentioned, which can remain workable for some 30 minutes in normal indoor light.

It would be desirable to have a command-curable composition which, despite comprising a number of dissimilar chemical compounds, was presented in a stable non-separating common solution and which, when set, did not tend to swell upon the absorption of water.

According to the present invention, a command-curable composition comprises (a) a partly esterified phosphonic acid being equivalent to the reaction product between a precursor of a polyphosphonic acid (e.g. poly(vinyl phosphonic acid)) and an esterifying group such as a polyhydric alcohol in the mole ratio (0.2–5.0) phosphonic acid groups: 1 esterifying group, (b) an initiator suitably a light-activated initiator system or a chemical initiator system, (c) cation-leachable glass powder, (d) poly(vinyl phosphonic acid) and is characterised by (e) a bulky molecule compatible with component (a) and having at least two vinyl groups through which it may cross-link/polymerise to yield a completely hydrophobic polymer. The composition preferably further comprises water. The said mole ratio is preferably (0.5–1.5):1 such as (0.8–1.2):1. The precursor may be vinyl phosphonic dichloride. The OH groups in the alcohol are preferably interconnected via from two to twenty such as two to six organic backbone (usually carbon atoms), with oxygen atoms optionally interposed at least (preferably) every fifth carbon atom. The bulky molecule may be a dimethacrylate such as a dimethacrylate formed from the reaction between bisphenol A and glycidyl methacrylate.

The cation-leachable (e.g. aluminosilicate) glass powder may be partly or wholly replaced by amphoteric or basic metal oxide (e.g. MgO, which may be de-activated at at least 900° C.). By "poly(vinyl phosphonic acid)" we include any multivalent-cation-catalysed cross-linkable polymeric acid containing on average one phosphonic acid group per one to three backbone carbon atoms. A minor proportion of poly(carboxylic acid) such as poly(acrylic acid) may also be present. This composition when mixed together will cure slowly by ionomer (acid-base) reaction between the phosphonic acid groups and the glass/oxide, and rapidly on demand by polymerising (cross-linking) reaction of the bulky molecule when initiated by (b).

The invention extends to a pack comprising the components of said composition (optionally excluding water) so presented as not to react prematurely, for example in the form of two separated pastes which when mixed form a curable composition as set forth above; the first paste may be the acid(s) plus water and the light-activated or ultrasound-activated initiator system, and the second paste may be the glass powder suspended in the dimethacrylate. If the two pastes have been formulated to appropriate concentrations, one could in use squeeze out equal lengths of paste from two tubes, or scoop out equal numbers of spoonfuls from two tubs, as an easy way to ensure that the mixture is of the correct composition.

The glass powder preferably consists of particles substantially all of which are smaller than 100 microns, preferably smaller than 60 microns. The Si:Al atomic ratio range of (0.6–2):1 yields an opaque product, which may be acceptable in appropriate cases, but (0.2–0.6):1 can also be used.

Also present may be fillers, preferably inert e.g. quartz, and/or a silanising agent to improve the incorporation of the filler into the cement. The bulky molecule can yield a completely hydrophobic polymer—thus stable against oral fluids—which can however successfully wet glass, improving the coherence of the set cement. The cement can also be compatible/adhesive to tooth material through phosphonate groups in the acid and in the esterified acid, the later being compatible with the bulky molecule yet itself being polar and thus hydophilic. The invention will now be described by way of example.

The components used in the following examples of light-cured, poly(vinyl phosphonic acid) glass ionomer cements are:

1. Bis GMA

Bis GMA is the main photopolymerisable component in the cement. It is a dimethacrylate resin formed from the reaction between bisphenol A and glycidyl methacrylate.

2. PR

PR is the product of reaction between vinyl phosphonyl dichloride and pentane 1,5 diol, as described in EP-A-395427. PR is another photopolymerisable component of the cement, although its degree of photopolymerisation is low for electronic reasons. Within the cement the PR should act as an adhesion promoter, also promoting compatibility and miscibility between the other components of the cement.

3. Initiator

This, the photopolymerisation initiator, is made up of camphorquinone (CQ), sodium toluenesulphinate (NaTS) and ethyl p-dimethylaminobenzoate (EDMAB). The components of the initiator are mixed in the ratio CQ:NaTS:EDMAB=0.3:2.0:0.75.

4. Water

Water is required in the cement formulation as the medium for ion transport in the acid-base reaction.

5. PVPA

PVPA is the polyacid, poly(vinyl phosphonic acid), used in the cement formulation. It is required for the conventional acid-base reaction in the cement formation.

6. Glass

The glass is an ion-leachable aluminosilicate. In the formation of the cement it acts as the base for the acid-base reaction. The glass is prepared by mixing together 437 parts by weight silica, 230 parts by weight alumina, 129 parts by weight calcium fluoride, 175 parts by weight cryolite and 29 parts by weight aluminium phosphate and heating to 1300° C. for 75 minutes. The melt is cooled rapidly by pouring into water. The resulting glass is ground and sieved, and the fraction of particle size less than 45 microns used in the composition.

For each example, the same mixing regime was followed:

All the components of the cement were weighed out ready. First the BisGMA and PR were combined on an inert surface. Then the Initiator was mixed in, followed by the Water and then the PVPA. When an homogeneous paste had been formed, the Glass was added as the final component. For the purposes of the determination of working time, time t=0 was taken as when the Glass was added.

Layered compressive strength specimens were prepared in 4×6 mm moulds; each layer was packed and then irradiated to cure it using dental blue light (35 W halogen lamp) as close as possible to the specimen but ensuring that the specimen did not touch the light. The cements were stored in the moulds at 37° C. for one hour and then stored in water at 37° C. for a further 23 hours. The load at failure in compression was measured using an Instron 1185 with crosshead speed 1 mm/min, from this value the measured compressive strength can be ascertained.

The duration of the irradiation to cure, the amount used of each component in parts by weight, and the resulting compressive strength in megaPascals (with the standard deviation), are shown for each Example in the following table.

| Ex No | cure | BisGMA | PR | Initr | Water | PVPA | Glass | CS | (sd) |
|---|---|---|---|---|---|---|---|---|---|
| 1 | 30s | 0.13 | 0.07 | 0.08 | 0.05 | 0.10 | 0.20 | 21.70 | (2.1) |
| 1a† | 30s | 0.13 | 0.07 | 0.08 | 0.05 | 0.10 | 0.20 | 15.76 | (1.6) |
| 2 | 30s | 0.13 | 0.07 | 0.09 | 0.05 | 0.10 | 0.30 | 18.30 | (4.7) |
| 2a† | 30s | 0.13 | 0.07 | 0.09 | 0.05 | 0.10 | 0.30 | 15.94 | (2.6) |
| 3 | 30s | 0.16 | 0.07 | 0.08 | 0.05 | 0.10 | 0.20 | 27.19 | (2.3) |
| 4 | 30s | 0.16 | 0.07 | 0.08 | 0.08 | 0.10 | 0.20 | 17.04 | (2.0) |
| 5 | 30s | 0.13 | 0.07 | 0.08 | 0.05 | 0.10 | 0.30 | 19.59 | (3.1) |
| 6 | 30s | 0.10 | 0.07 | 0.08 | 0.05 | 0.10 | 0.20 | 9.78 | (1.8) |
| 7 | 40s | 0.13 | 0.07 | 0.06 | 0.05 | 0.10 | 0.20 | 17.97 | (2.0) |
| 8 | 40s | 0.13 | 0.07 | 0.06 | 0.05 | 0.10 | 0.30 | 33.58 | (5.3) |
| 9 | 30s | 0.16 | 0.07 | 0.08 | 0.05 | 0.10 | 0.30 | 23.10 | (4.9) |
| 10 | 30s | 0.16 | 0.07 | 0.08 | 0.05 | 0.10 | 0.40 | 30.90 | (3.3) |
| 10a | 40s | 0.16 | 0.07 | 0.08 | 0.05 | 0.10 | 0.40 | 34.53 | (4.9) |
| 11 | 30s | 0.16 | 0.07 | 0.08 | 0.05 | 0.10 | 0.45 | 29.00● | (7.5) |
| 11a | 30s | 0.16 | 0.07 | 0.08 | 0.05 | 0.10 | 0.45 | 30.60 | (2.6) |
| 11b | 40s | 0.16 | 0.07 | 0.08 | 0.05 | 0.10 | 0.45 | 31.45 | (3.2) |
| 12 | 30s | 0.16 | 0.07 | 0.08 | 0.05 | 0.10 | 0.50 | 30.98 | (6.1) |
| 12a | 40s | 0.16 | 0.07 | 0.08 | 0.05 | 0.10 | 0.50 | 32.92 | (3.9) |
| 13 | 30s | 0.13 | 0.07 | 0.08 | 0.075 | 0.15 | 0.45 | 23.28 | (3.3) |
| 14 | 30s | 0.13 | 0.07 | 0.08 | 0.075 | 0.15 | 0.55 | 26.44 | (1.6) |
| 15 | 30s | 0.20 | 0.07 | 0.08 | 0.05 | 0.10 | 0.55 | 38.67* | (4.0) |
| 15a | 40s | 0.20 | 0.07 | 0.08 | 0.05 | 0.10 | 0.55 | 41.74▽ | (4.6) |
| 15b§ | 30s | 0.20 | 0.07 | 0.08 | 0.05 | 0.10 | 0.55 | 34.87 | (5.0) |

Notes
†stored in air
§storage: in mould 37° C. 1 hr; in moist atmosphere 37° C. for further 23 hrs; in water 37° C. for next 24 hrs
●high value recorded 43.34 MPa
*high value recorded 45.83 MPa
▽high value recorded 49.67 MPa The wide variation in these compressive strength values may be due to various extraneous factors, such as the difficulty in consistently packing layers in the mould (specimens yielding lower strengths when there were obvious flaws in the sides of the specimen) and the time elapsed between mixing and placing, and irradiating, during which time a glass ionomer matrix may have formed to a sufficient extent to impede formation of the polymerisation matrix. If this is the case then the two matrix forming reactions are in competition. Consequently it is possible that difference layers within the same cement may have different proportions of acid-base and polymerisation matrices and hence different strengths.

The presence of PVPA (preferably at least 1¼, e.g. at least twice, the mass of the water) and of the PR should improve the adhesion of the cement to tooth material. BisGMA undergoes the main light-induced polymerisation and is used in this formulation because it has a good percentage conversion on illumination and also because as a result of its bulky size the hydrophilicity and polymerisation shrinkage are small.

Effect of BisGMA

Comparing Examples 1, 3 and 6 shows that increasing the levels of BisGMA increased the strength of the cement. It was preferably at least 1½ times, more preferably at least twice the mass of the PVPA.

Effect of Level of Initiator

It is important that the level of initiator be as low as possible in the cement, otherwise the components of the initiator can leach our from the set cement and cause a cytotoxic response. A reduction in the level of initiator may need to be accompanied by an increase in irradiation time, which is allowable provided that the longer irradiation time is still acceptable clinically. Examples 1, 2 and 7 suggest an optimum around 13% by mass of initiator, which is high.

Effect of Cure Time

Increasing the cure time of the material did not appear to cause a statistically significant increase in strength for Examples 10/10a, 11/11b, 12/12a nor 15/15a. This would imply that for these materials the 30 seconds' cure time is sufficient.

Effect of Level of Glass

The glass acts as both the filler in the photopolymerisation reaction and the base in the acid-base reaction. While increasing the level of glass in the system should improve the strength of the cement, Examples 9, 10, 11 and 12 show a trend which is not significant statistically. Glass was preferably more than four, more preferably more than five, times the mass of the PVPA, especially advantageously with high bisGMA.

BisGMA, being a dimethacrylate resin formed from the reaction between bisphenol A and glycidyl methacrylate, has the structure

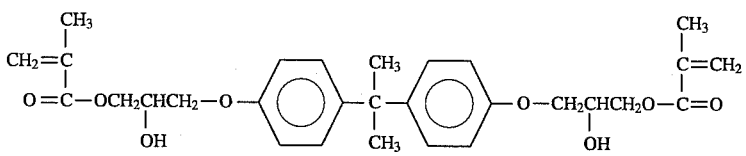
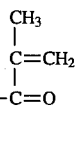

Hydroxyethylmethacrylate (HEMA), a significantly smaller molecule, has the structure

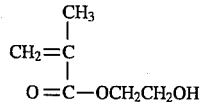

Both are polymerised through the vinyl ($CH_2=C<$) group. Dimethacrylates such as bisGMA give crosslinked polymers, while HEMA forms linear polymers which may however show branching.

We claim:

1. A command-curable composition comprising:
   (a) a partly esterified phosphonic acid being equivalent to the reaction product between a precursor of a poly(vinyl phosphonic acid) and a polyhydric alcohol, in the mole ratio (0.2–5.0) phosphonic acid groups: 1 esterifying group;
   (b) an initiator;
   (c) cation-leachable glass powder and/or amphoteric or basis metal oxide;
   (d) poly(vinyl phosphonic acid); and
   (e) a bulky molecule compatible with component (a) and having at least two vinyl groups through which it may cross-link/polymerize to yield a completely hydrophobic polymer, said bulky molecule being a dimethacrylate;

said partly esterified phosphonic acid (a) being present in an amount to promote adhesion and to promote compatibility and miscibility of the other components of the composition;

the weight ratio of component (d) to component (c) being from 1:2 to 1:5.5; and the weight ratio of component (d) to component (a)+ component (e) being from 1:1.3 to 1:2.7.

2. A command-curable composition according to claim 1, further comprising water.

3. A command-curable composition according to claim 1, wherein the OH groups in the alcohol are interconnected via from two to twenty organic backbone atoms.

4. A command-curable composition according to claim 3, wherein the OH groups in the alcohol are interconnected via carbon atoms with oxygen atoms interposed at least every fifth carbon atom.

5. A command-curable composition according to claim 3, wherein the said mole ratio is (0.5–1.5):1.

6. A command-curable composition according to claim 5, wherein the said mole ratio is (0.8–1.2):1.

7. A command-curable composition according to claim 1, wherein the said precursor is vinyl phosphonic dichloride.

8. A command-curable composition according to claim 1, wherein component (c) is aluminosilicate glass powder.

9. A command-curable composition according to claim 8, wherein the glass powder (c) has an Si:Al atomic ratio of (0.2–0.6):1 or (0.6–2):1.

10. A command-curable composition according to claim 1, wherein the glass powder consists of particles substantially all of which are smaller than 100 microns.

11. A command-curable composition according to claim 1, wherein component (c) is MgO deactivated at at least 900° C.

12. A command-curable composition according to claim 1, further comprising a filler.

13. A command-curable composition according to claim 1, further comprising a silanizing agent.

14. A pack comprising all the components of a composition according to claim 1, so presented as not to react prematurely.

* * * * *

UNITED STATES PATENT AND TRADEMARK OFFICE
CERTIFICATE OF CORRECTION

PATENT NO. : 5,601,640
DATED      : February 11, 1997
INVENTOR(S) : Anstice, et. al.

It is certified that error appears in the above-identified patent and that said Letters Patent is hereby corrected as shown below:

Title page, items [86] and [87]

delete "PCT/GB87/00085" and replace by --PCT/GB93/02238--;

delete "WO88/05651" and replace by --WO94/09748-- delete "Aug. 11, 1988" and replace by --May 11, 1994--

Signed and Sealed this

Thirteenth Day of January, 1998

BRUCE LEHMAN

Attest:

Attesting Officer

Commissioner of Patents and Trademarks